United States Patent [19]

DeWitt et al.

[11] Patent Number: 5,723,676
[45] Date of Patent: Mar. 3, 1998

[54] PROCESS FOR PRODUCING BENZOPHENONE COMPOUNDS

[75] Inventors: Lee Alan DeWitt; Heng Su; Chempolil Thomas Mathew, all of Morris County, N.J.

[73] Assignee: AlliedSignal Inc., Morristown, N.J.

[21] Appl. No.: 674,293

[22] Filed: Jul. 1, 1996

[51] Int. Cl.[6] .................................................. C07C 45/42
[52] U.S. Cl. ..................................... 568/323; 568/309
[58] Field of Search ................................. 568/306, 309, 568/323

[56] References Cited

U.S. PATENT DOCUMENTS

| | | | |
|---|---|---|---|
| 3,641,132 | 2/1972 | Schulz et al. | 568/306 |
| 3,642,906 | 2/1972 | Krasha | 260/591 |
| 3,692,652 | 9/1972 | Sevferth et al. | 204/158 |
| 4,124,726 | 11/1978 | Hamazaki et al. | 424/331 |
| 4,263,458 | 4/1981 | Bowden et al. | 568/323 |
| 4,297,514 | 10/1981 | Ma | 568/309 |
| 4,405,523 | 9/1983 | Fields | 260/369 |
| 4,978,798 | 12/1990 | Stults | 568/316 |

FOREIGN PATENT DOCUMENTS

| | | | |
|---|---|---|---|
| 89168/82 | 1/1983 | Australia | 568/321 |

*Primary Examiner*—James H. Reamer
*Attorney, Agent, or Firm*—Lois A. Gianneschi; Jay P. Friedenson

[57] ABSTRACT

A process for producing benzophenone compounds is provided. Specifically, a process is provided for producing benzophenone compounds in which a diphenylmethane compound is reacted with manganese dioxide and a strong acid. The process yields the product benzophenone in high purity and good yield.

24 Claims, No Drawings

PROCESS FOR PRODUCING BENZOPHENONE COMPOUNDS

FIELD OF THE INVENTION

This invention relates to a process for producing benzophenone compounds. In particular, a process is provided for producing benzophenone compounds, in good yield and with high purity, in which a diphenylmethane compound is reacted with manganese dioxide and a strong acid.

BACKGROUND OF THE INVENTION

Benzophenone compounds find utility in a variety of applications. For example, the compound 4,4'-difluorobenzophenone is used as a reactant in the production of aromatic polyketone polymers and in the synthesis of pharmaceutical products.

A number of methods are known for the production of benzophenone compounds. U.S. Pat. No. 3,642,906 discloses the homogeneous catalytic oxidation of a diphenylmethane compound in the presence of copper naphthenate to produce benzophenone compounds, including 4,4'-dimethylbenzophenone. The process has several disadvantages including high reaction temperatures of 185° to 220° C. and long reaction times of up to 28 hours, use of a toxic metal reagent, difficulty in separating the organic-soluble metal catalyst, and low conversion with yields of only up to 72 percent.

U.S. Pat. No. 4,263,458 discloses a process for producing 4,4'-difluorobenzophenone in which sodium nitrite and hydrogen fluoride are used to react with methylene dianiline. The process is disadvantageous in that the fluoride salt produced is explosive and processing is difficult.

U.S. Pat. No. 4,978,798 discloses a process for making 4,4'-difluorobenzophenone by reacting a trimethylhalobenzene with a halobenzene and a Lewis acid to form a bishalophenyl dihalomethane, which is then reacted with water to form the halobenzophenone. The non-fluorine halogen atoms of the halobenzophenone subsequently are removed in a step that uses a noble metal catalyst. This process is disadvantageous in that it is a multi-step process requiring purification of the product intermediates.

Also known is the Friedel-Crafts reaction of fluorobenzene with carbon tetrachloride in aluminum fluoride for the synthesis of 4,4'-difluorobenzophenone. 30 Eur. Poly. J., 1381–88 (1994). Although a general procedure for the synthesis of benzophenones, the Freidel-Crafts process is disadvantageous in this case because there is a significant amount of isomeric byproduct, 2,4'-difluorobenzophenonone, produced.

Thus, a need exists in the art for a process for producing benzophenone compounds economically, efficiently, and safely. The present invention provides a process for producing benzophenone compounds in high purity and good yield that overcomes some of the disadvantages of the prior art methods.

DESCRIPTION OF THE PREFERRED EMBODIMENT

The invention provides an efficient and economical method for producing a benzophenone compound in high purity and good yield. By the term benzophenone compound is meant unsubstituted, monosubstituted and disubstituted benzophenone compounds.

The process of the invention comprises: (A) mixing a diphenylmethane compound with an effective amount of a first reactant and sufficient water to form a slurry; (B) heating the slurry; (C) adding an effective amount of a second reactant to the heated slurry to form a reaction mixture; (D) reacting the reaction mixture at a temperature and for a time sufficient to form a reaction product comprising a benzophenone product and reaction byproducts; (E) separating the benzophenone product from the reaction byproducts; and (F) purifying the benzophenone product in order to obtain a purified benzophenone compound.

In another embodiment, the process of the invention comprises: (A) mixing a disubstituted diphenylmethane compound with an effective amount of a first reactant and sufficient water to form a slurry; (B) heating the slurry; (C) adding an effective amount of a second reactant to the heated slurry to form a reaction mixture; (D) reacting the reaction mixture at a temperature and for a time sufficient to form a reaction product comprising a disubstituted benzophenone product and reaction byproducts; (E) separating the disubstituted benzophenone product from the reaction byproducts; and (F) purifying the disubstituted benzophenone product in order to obtain a purified disubstituted benzophenone compound.

In yet another embodiment of the invention, a method for producing 4,4'-difluorobenzophenone is provided comprising: (A) mixing 4,4'-difluorodiphenylmethane with an effective amount of a first reactant and sufficient water to form a slurry; (B) heating the slurry; (C) adding an effective amount of a second reactant to the heated slurry to form a reaction mixture; (D) reacting the reaction mixture at a temperature and for a time sufficient to form a reaction product comprising a 4,4'-difluorobenzophenone product and reaction byproducts; (E) separating the 4,4'-difluorobenzophenone product from the reaction byproducts; and (F) purifying the 4,4'-difluorobenzophenone product in order to obtain purified 4,4'-difluorobenzophenone.

The process of the invention may be carried out in batch or continuous mode. The process is carried out in any suitable corrosion resistant vessel such as a glass-lined, polytetrafluoroethylene-lined, or stainless steel reactor.

The diphenylmethane compounds useful in the process of the invention are of the formula: $(X_pC_6H_{5-p})CH_2(C_6H_{5-p}X_p)$ in which X is fluorine, chlorine, bromine, or iodine and p is 0 or 1. Preferably, 4,4'-difluorodiphenylmethane is used.

The reactants useful in the process of the invention are manganese dioxide and a strong acid. When manganese dioxide is used as the first reactant, the strong acid is used as the second reactant. Conversely, when the first reactant is a strong acid, the second reactant is manganese dioxide.

The manganese dioxide useful in the invention may be any commercially available manganese dioxide, which compound comes in a variety of grades and purities. Generally, the manganese dioxide used is at least 50 percent pure. Preferably, the manganese dioxide is from about 80 to about 100, more preferably from about 80 to about 85, percent pure. Alternatively, mineral grade manganese dioxide directly from the mine may be used, which manganese dioxide is about 80 to about 85 percent pure. An effective amount of manganese dioxide is an amount effective to oxidize the methane functionality of the diphenylmethane compound to the ketone. The amount of manganese dioxide used in the process of the invention is, generally, an mount from about 2 to about 7 moles per mole of diphenylmethane compound. Preferably from about 3 to about 5 moles per mole diphenylmethane compound is used.

The strong acids useful in the invention are any acids having a pH of about 4 or less. Suitable such acids include, without limitation, hydrochloric, sulfuric, and nitric acid. Preferably, sulfuric or hydrochloric acid is used. The acid may be used in dilute or concentrated forms. Generally, an effective amount of the strong acid is an amount effective to promote oxidation of the methane functionality of the diphenylmethane compound to the ketone. Preferably, the amount of acid used is from about 2 to about 20 moles per mole of diphenylmethane compound, more preferably from about 5 to about 10 moles is used. Conversion of the diphenylmethane compound to the desired product is related to the rate of acid addition. Preferably, addition takes place at from about 0.01 equivalents/min to about 10 equivalents/min.

In step (A) of the process of the invention, an effective amount of a first reactant and the diphenylmethane are mixed with water in order to form a slurry. The amount of water used is an amount sufficient to form a slurry. Generally, from about 0 to about 3 parts water per 1 part diphenylmethane compound is used. Preferably, from about 1 to about 2, more preferably about 1.5 parts water is used.

In step (B), the slurry formed in step (A) is heated. The slurry is heated to a temperature from about 70° to about 200° C., preferably, from about 90° to about 100° C. In step (C), an effective amount of a second reactant is added to the heated slurry in order to form a reaction mixture.

The reaction mixture is then reacted in step (D) at a temperature and for a time sufficient to form a reaction product comprising a benzophenone product and reaction byproducts. The reaction temperature may be from about 70° to about 200° C., preferably from about 90° to about 140° C. The higher the reaction temperature, the faster the reaction will proceed and, thus, higher reaction temperatures may be desirable in comparison to the lower temperatures. The pressure at which the reaction proceeds is not critical, atmospheric and superatmospheric pressures being preferred for convenience sake. The reaction time will depend on the amount of manganese dioxide, acid, and temperature selected. Generally, the reaction time will be from about 1 to about 15 hours.

Reacting of the reaction mixture forms a reaction product comprising benzophenone product, trace amounts of organic byproducts and inorganic reaction byproducts, unreacted manganese dioxide, and unreacted diphenylmethane compound. In step (E), the benzophenone product is separated from the reaction byproducts. Separation may be performed by any known means and conveniently is performed by simple filtration in which a solvent is added to the benzophenone product and the unreacted manganese dioxide, along with any other insolubles, is filtered out. Suitable solvents include, without limitation, toluene, xylenes, hexane, chlorobenzene, and mixture thereof. Preferably, toluene is used. The solvent is used in a ratio of parts solvent to parts product of from about 1:1 to about 10:1, more preferably from about 2:1 to about 4:1, most preferably about 3:1.

The benzophenone product is purified in step (F) by any known means. Conveniently, the benzophenone product is purified by evaporation of the solvent and recrystallization to produce a purified benzophenone compound.

The purified benzophenone compound will be, at a minimum, approximately 92 percent pure. Further, because only a small amount, approximately less than 1 percent, of organic byproducts is formed and conversion of the diphenylmethane compound is substantially complete, the process of the invention provides high purity benzophenone compounds in good yield.

The following illustrative examples will further clarify the invention.

EXAMPLES

Example 1

To a 250 mL round bottomed flask equipped with a heating mantle, overhead agitator, thermometer, condenser, and addition funnel with a tube protruding below the liquid level was added 10.6 g 4,4'-difluorodiphenylmethane (0.051 moles). Agitation was begun and a slurry of 20.5 g $MnO_2$ (0.195 moles) in 30 g water was added to the flask. About 30 g of water were used to wash the $MnO_2$ beaker and were added to the flask. The mixture was allowed to reach about 100° C. at which point 50 g $H_2SO_4$ (0.487 moles) were added to the addition funnel. The $H_2SO_4$ was then added dropwise into the flask and the reaction temperature slowly rose to about 125° C. when all of the acid had been added. The mixture was heated to maintain the temperature at about 125° C. until gas chromatography showed complete conversion after approximately 12 hours. The reaction mixture was allowed to cool to 100° C. and 50 g toluene were added to the mixture. A slurry of 6 g diatomaceous earth in 30 g water was poured into a vacuum Buchner funnel fitted with No. 42 filter paper to form a filter pre-coat. The contents of the round bottomed flask were then vacuum filtered. 10 g toluene was used to wash the flask and, subsequently, the filter cake. The filter cake was then washed with 100 g toluene heated to about 50° to 70° C. and the filtrate phase separated. The toluene was removed from the organic phase by heating to approximately 65° C. at 10 mm Hg. The 10 g yellow solids assayed as 95% pure 4,4'-difluorobenzophenone for an 84% yield. The solids were recrystallized from a hexane solvent leaving 7.7 g crystalline 4,4'-difluorobenzophenone for a 68% yield.

Example 2

The procedure of Example 1 was used except that 20 g 4,4'-difluorodiphenylmethane, 30 g water, 31 g $MnO_2$ and 50 g $H_2SO_4$ were used. 20 g off-white solids, after toluene removal, afforded 95% pure 4,4'-difluorobenzophenone in a 90% yield.

Example 3

The procedure of Example 2 was used except that recrystallization was performed using isopropanol. The yield was 77% 4,4'-difluorobenzophenone that was 99% pure.

Example 4

To a 250 mL round bottomed flask equipped with a heating mantle, overhead agitator, thermometer, condenser and addition funnel with a tube protruding below the liquid level was added 20.0 g 4,4'-difluorodiphenylmethane (0.098 moles). Agitation was begun and a slurry of 31 g $MnO_2$ (0.303 moles) in 30 g water was added to the flask. The mixture was allowed to reach about 100° C. at which point 95 g, 37%, HCl (1.0 mole) were added to the addition funnel. The HCl was then added dropwise into the flask and the reaction temperature slowly rose to about 108° C. when all of the acid had been added. The mixture was heated to maintain the temperature at about 108° C. until gas chromatography showed 95% conversion after approximately 3 hours. 50 g toluene were added to the reaction mixture, the contents of the round bottomed flask were then vacuum filtered. 10 g toluene were used to wash the flask and, subsequently, the filter cake. The filter cake was then washed with 100 g toluene heated to about 50° to 70° C. and the filtrate phase separated, the toluene was removed from the organic phase by heating to approximate 65° C. at 10 mm Hg. The 20 g off-white solids assayed as 95% pure 4,4'-difluorobenzophenone.

Example 5

The procedure of Example 4 was used except that recrystallization was performed using isopropanol. The yield was 75% 4,4'-difluorobenzophenone that was 99% pure.

Example 6

The procedure of Example 2 was used except that 15.6 g diphenylmethane was used. The yield was 62% benzophenone that is 95% pure.

Example 7

To a 250 mL round bottomed flask equipped with a heating mantle, overhead agitator, thermometer, condenser and addition funnel with a tube protruding below the liquid level was added 20.0 g 4,4'-difluorodiphenylmethane (0.098 moles). Agitation was begun and a slurry of 30.0 g $MnO_2$ (0.293 moles) in 30 g water was added to the flask. The mixture was allowed to reach about 100° C. at which point 70 g, 90%, $HNO_3$ (1.0 mole) were added to the addition funnel. The $HNO_3$ was then added dropwise into the flask and the reaction temperature slowly rose to about 122° C. when all of the acid had been added. The mixture was heated to maintain the temperature at about 122° C. until gas chromatography showed 100% conversion after approximately 2 hours. The reaction mixture was allowed to cool to about 100° C. and 50 g toluene were added to the reaction mixture. the contents of the round bottomed flask were then vacuum filtered. 10 g toluene were used to wash the flask and, subsequently, the filter cake. The filter cake was then washed with 100 g toluene heated to about 50° to 70° C. and the filtrate phase separated. the toluene was removed from the organic phase by heating to approximately 65° C. at 10 mm Hg. The 20 g yellow solids assayed as 95% pure 4,4'-difluorobenzophenone for a 90% yield.

Example 8

The procedure of Example 7 was used except that recrystallization was performed using isopropanol. The yield was 80% 4,4'-difluorobenzophenone that was 99% pure.

Example 9

The procedure of Example 2 is used except that the 4,4'-difluorodiphenylmethane, water, and sulfuric acid are first mixed, then heated before the $MnO_2$ is added. The yield is 54% 4,4'-difluorobenzophenone that is 95% pure.

Example 10

The procedure of Example 2 is used except that 22.7 g 4,4'-dichlorodiphenylmethane is used. The yield is 79% 4,4'-dichlorobenzophenone that is 93% pure.

Example 11

The procedure of Example 2 is used except that 31.6 g 4,4'-dibromodiphenylmethane is used. The yield is 74% 4,4'-dibromobenzophenone that is 96% pure.

Example 12

The procedure of Example 2 is used except that 41.0 g 4,4'-diiododiphenylmethane is used. The yield is 69% 4,4'-diiodobenzophenone that is 94% pure.

What is claimed is:

1. A process for producing a benzophenone compound comprising the steps of:

(A) mixing a diphenylmethane compound of the formula: $(X_pC_6H_{5-p})CH_2(C_6H_{5-p}X_p)$ wherein X is fluorine, chlorine, bromine, or iodine and p is 0 or 1 with an effective amount of a first reactant and a sufficient amount of water to form a slurry;

(B) heating the slurry formed in step (A);

(C) adding an effective amount of a second reactant to the heated slurry in order to form a reaction mixture;

(D) reacting the reaction mixture at a temperature of from about 70° to about 200° C. and for a time sufficient to form a reaction product comprising a benzophenone product and reaction byproducts;

(E) separating the benzophenone product from the reaction byproducts; and (F) purifying the benzophenone product in order to obtain a purified benzophenone compound wherein the first and second reactant are selected from the group consisting of manganese dioxide and a strong acid, provided that if the first reactant is manganese dioxide the second reactant is the strong acid and if the first reactant is the strong acid, the second reactant is manganese dioxide and wherein the amount of the strong acid is an amount of from about 2 to about 20 moles per mole of the diphenylmethane compound.

2. The process of claim 1 wherein the diphenylmethane compound is 4,4'-difluorodiphenylmethane and the benzophenone product is 4,4'-difluorobenzophenone.

3. The process of claim 1 wherein the strong acid is an acid having a pH of about 4 or less.

4. The process of claim 3 wherein the acid is sulfuric acid, nitric acid, or hydrochloric acid.

5. The process of claim 3 wherein the acid is sulfuric acid.

6. The process of claim 3 wherein the acid is hydrochloric acid.

7. The process of claim 3 wherein the acid is nitric acid.

8. The process of claim 1 wherein the manganese dioxide is mineral grade manganese dioxide.

9. The process of claim 1 wherein the strong acid is added at a rate from about 0.01 equivalents/min to about 10 equivalents/min.

10. A process for producing a benzophenone compound comprising the steps of:

(A) mixing a disubstituted diphenylmethane compound of the formula: $(X_pC_6H_{5-p})CH_2(C_6H_{5-p}X_p)$ wherein X is fluorine, chlorine, bromine, or iodine and p is 0 or 1, an effective amount of a first reactant and from about 0 to about 3 parts water per part of the disubstituted diphenylmethane compound to form a slurry;

(B) heating the slurry formed in step (A) to from about 70° to about 200° C.;

(C) adding an effective amount of a second reactant to the heated slurry in order to form a reaction mixture;

(D) reacting the reaction mixture at a temperature from about 70° C. to about 200° C. and for a time from about 1 to about 15 hours to form a reaction product comprising a disubstituted benzophenone product and reaction byproducts;

(E) separating the disubstituted benzophenone product from the reaction byproducts; and (F) purifying the disubstituted benzophenone product in order to obtain a purified disubstituted benzophenone compound wherein the first and second reactant are selected from the group consisting of manganese dioxide and a strong acid, provided that if the first reactant is manganese dioxide the second reactant is the strong acid and if the first reactant is the strong acid, the second reactant is manganese dioxide and wherein the mount of the strong acid is an amount of from about 2 to about 20 moles per mole of the disubstituted diphenylmethane compound.

11. The process of claim 10 wherein the manganese dioxide is used in an amount of from about 2 to about 7 moles per mole of the disubstituted diphenylmethane compound.

12. The process of claim 11 wherein the strong acid is added at a rate of from about 0.01 equivalents/min to about 10 equivalents/min.

13. The process of claim 10 wherein the disubstituted diphenylmethane compound is 4,4'-difluorodiphenylmethane and the disubstituted benzophenone product is 4,4'-difluorobenzophenone.

14. The process of claim 12 wherein the strong acid is sulfuric acid, nitric acid, or hydrochloric acid.

15. The process of claim 14 wherein the acid is sulfuric acid.

16. The process of claim 14 wherein the acid is hydrochloric acid.

17. The process of claim 14 wherein the acid is nitric acid.

18. The process of claim 11 wherein the manganese dioxide is mineral grade manganese dioxide.

19. A process for producing 4,4'-difluorobenzophenone comprising the steps of:

(A) mixing 4,4'-difluorodiphenylmethane, an effective amount of a first reactant and from about 0 to about 3 parts water per part of the 4,4'-difluorodiphenylmethane to form a slurry;

(B) heating the slurry formed in step (A) to from about 90° to about 100° C.;

(C) adding an effective mount of a second reactant to the heated slurry in order to form a reaction mixture;

(D) reacting the reaction mixture at a temperature from about 90° C. to about 140° C. and for a time from about 1 to about 15 hours to form a reaction product comprising a 4,4'-difluorobenzophenone product and reaction byproducts;

(E) separating the 4,4'-difluorobenzophenone product from the reaction byproducts; and (F) purifying the 4,4'-difluorobenzophenone product in order to obtain purified 4,4'-difluorobenzophenone wherein the first and second reactant are selected from the group consisting of manganese dioxide and a strong acid, provided that if the first reactant is manganese dioxide the second reactant is the strong acid and if the first reactant is the strong acid, the second reactant is manganese dioxide and wherein the amount of the strong acid is an amount of from about 2 to about 20 moles per mole of the 4,4'-difluorodiphenylmethane compound.

20. The process of claim 19 wherein the manganese dioxide is used in an amount of from about 3 to about 5 moles per mole of the 4,4'-difluorodiphenylmethane and the strong acid is an acid having a pH of about 4 or less, the acid selected from the group consisting of sulfuric acid, nitric acid and hydrochloric acid and added at a rate from about 0.01 equivalents/min to about 10 equivalents/min and in an amount of from about 5 to about 10 moles per mole of the 4,4'-difluorodiphenylmethane.

21. The process of claim 20 wherein the acid is sulfuric acid.

22. The process of claim 20 wherein the acid is hydrochloric acid.

23. The process of claim 20 wherein the acid is nitric acid.

24. The process of claim 20 wherein the manganese dioxide is mineral grade manganese dioxide.

* * * * *